(12) United States Patent
Jeong et al.

(10) Patent No.: US 12,275,698 B2
(45) Date of Patent: Apr. 15, 2025

(54) METHOD OF PREPARING DIESTER-BASED MATERIAL

(71) Applicant: LG CHEM, LTD., Seoul (KR)

(72) Inventors: Jae Hun Jeong, Daejeon (KR); Sung Kyu Lee, Daejeon (KR); Yeon Uk Choo, Daejeon (KR); Song Hoon Lee, Daejeon (KR); Hyoung Jun, Daejeon (KR); Yun Gon Heo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 601 days.

(21) Appl. No.: 17/635,925

(22) PCT Filed: Aug. 20, 2021

(86) PCT No.: PCT/KR2021/011084
§ 371 (c)(1),
(2) Date: Feb. 16, 2022

(87) PCT Pub. No.: WO2022/108050
PCT Pub. Date: May 27, 2022

(65) Prior Publication Data
US 2022/0371984 A1    Nov. 24, 2022

(30) Foreign Application Priority Data

Nov. 17, 2020    (KR) .......................... 10-2020-0153956

(51) Int. Cl.
| C07C 67/08 | (2006.01) |
| C07C 67/58 | (2006.01) |
| C07C 69/82 | (2006.01) |

(52) U.S. Cl.
CPC .............. *C07C 67/08* (2013.01); *C07C 67/58* (2013.01); *C07C 69/82* (2013.01)

(58) Field of Classification Search
CPC ......... C07C 67/08; C07C 67/58; C07C 67/54; C07C 69/54; C07C 69/82
See application file for complete search history.

(56) References Cited

U.S. PATENT DOCUMENTS

| 5,095,138 A | 3/1992 | Labat et al. |
| 6,812,321 B1 | 11/2004 | Heitz et al. |

(Continued)

FOREIGN PATENT DOCUMENTS

| CN | 1118158 A | 3/1996 |
| CN | 1478115 A | 2/2004 |

(Continued)

OTHER PUBLICATIONS

Office Action issued in related Chinese Patent Application No. 202180005264.4 dated Aug. 25, 2023.

(Continued)

*Primary Examiner* — Yate' K Cutliff
(74) *Attorney, Agent, or Firm* — Morgan, Lewis & Bockius LLP

(57) ABSTRACT

A diester-based material can be prepared continuously including a reaction part in which a total of n reaction units from a first reaction unit to an nth reaction unit are connected in series, the reaction unit including a reactor which esterifies dicarboxylic acid and alcohol, includes: esterifying dicarboxylic acid and alcohol in a reactor of the first reaction unit to produce a reaction product, and supplying a lower discharge stream including the reaction product to a reaction unit at a rear end, wherein an operating pressure of the reactor of the first reaction unit is 0.4 kg/cm$^2$G to 5.5 kg/cm$^2$G, an operating pressure is reduced from a reactor of any one reaction unit of reaction units from a second reaction unit to the nth reaction unit, and an operating (Continued)

temperature is increased from the reactor of the first reaction unit to the reactor of the nth reaction unit.

11 Claims, 1 Drawing Sheet

(56) References Cited

U.S. PATENT DOCUMENTS

| | | | |
|---|---|---|---|
| 2001/0031231 | A1 | 10/2001 | Nakamoto et al. |
| 2006/0252960 | A1 | 11/2006 | Sohn et al. |
| 2007/0161815 | A1 | 7/2007 | Osborne et al. |
| 2008/0033084 | A1 | 2/2008 | Bashir et al. |
| 2010/0137631 | A1 | 6/2010 | De Munck |
| 2011/0251420 | A1* | 10/2011 | Disteldorf ............... C07C 67/08 560/99 |
| 2016/0264509 | A1* | 9/2016 | Kaller ..................... C07C 67/08 |
| 2019/0263745 | A1 | 8/2019 | Lee et al. |
| 2021/0317063 | A1 | 10/2021 | Lee et al. |

FOREIGN PATENT DOCUMENTS

| | | |
|---|---|---|
| CN | 102295564 A | 12/2011 |
| CN | 102442905 A | 5/2012 |
| CN | 107935846 B | 1/2020 |
| EP | 3 854 776 A1 | 7/2021 |
| JP | 2012-512229 A | 5/2012 |
| JP | 2018-052993 A | 4/2018 |
| KR | 10-0351783 B1 | 9/2002 |
| KR | 10-2005-0089055 A | 9/2005 |
| KR | 10-0610299 B1 | 8/2006 |
| KR | 10-2009-0115125 A | 11/2009 |
| KR | 10-2009-0130042 A | 12/2009 |
| KR | 10-2011-0101205 A | 9/2011 |
| KR | 10-1152510 B1 | 6/2012 |
| KR | 10-1663586 B1 | 10/2016 |
| KR | 10-2019-0027623 A | 3/2019 |
| KR | 10-1965415 B1 | 4/2019 |
| KR | 10-2020-0063577 A | 6/2020 |
| KR | 10-2162204 B1 | 10/2020 |
| WO | 2020/204558 A1 | 10/2020 |

OTHER PUBLICATIONS

Extended European Search Report dated Aug. 23, 2023, issued in corresponding European Patent Application No. 21854731.3.
International Search Report and Written Opinion issued in corresponding International Patent Application No. PCT/PCT/KR2021/011084, dated Jan. 12, 2021.

* cited by examiner

[FIG. 1]
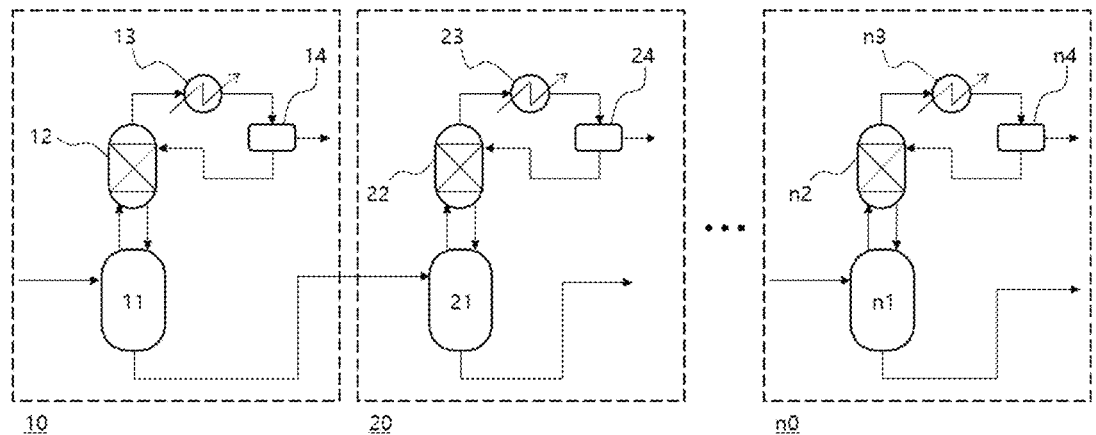
[FIG. 2]
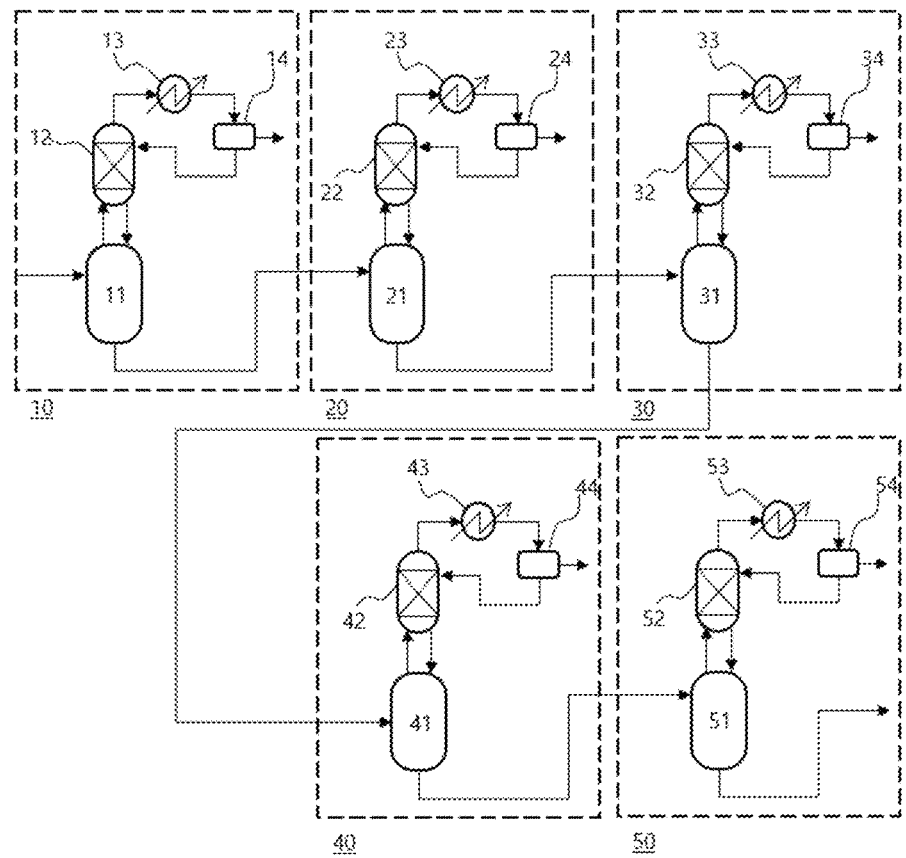

METHOD OF PREPARING DIESTER-BASED MATERIAL

CROSS-REFERENCE TO RELATED APPLICATIONS

The present application claims the benefit of priority to Korean Patent Application No. 10-2020-0153956, filed on Nov. 17, 2020, the entire contents of which are incorporated herein as a part of the specification.

TECHNICAL FIELD

The present invention relates to a method of preparing a diester-based material, and more particularly, to a method of preparing diester-based material which may improve productivity of a diester-based material by controlling a reaction rate of a reactant while minimizing an amount of energy used which is supplied to a reactor when continuously preparing a diester-based material.

BACKGROUND ART

A phthalate-based plasticizer, which accounts for 92% of the global plasticizer market until the 20th century, and is an additive mainly used for imparting flexibility, durability, cold resistance, and the like to polyvinyl chloride (PVC) and lowering melt viscosity to improve processability, is introduced to PVC at various contents to be more closely related to real life than any other materials, ranging from hard products such as hard pipes to soft products which may be used for food packaging, blood bags, flooring, and the like which are soft and stretch easily, and to be widely used as an application in which a direct contact with a human body is inevitable.

However, in spite of the compatibility with PVC and excellent softness imparting properties of the phthalate-based plasticizer, recently, controversy over harmfulness that in the real use of a PVC product containing the phthalate-based plasticizer, the phthalate-based plasticizer may leak out of the product little by little to act as a suspected endocrine disruptor (environmental hormone) and a carcinogen at a heavy metal level is rising. In particular, since it was reported that di-(2-ethylhexyl) phthalate (DEHP) which is the most used among the phthalate-based plasticizers in the US in the 1960s leaks out of a PVC product, interest in environmental hormones increased in the 1990s and various studies on harmfulness of the phthalate-based plasticizer to a human body began to be conducted.

Thus, research for developing an environment-friendly plasticizer for replacing di(2-ethylhexyl)phthalate and improving the process is being conducted by many researches, in order to respond to environmental hormone problems and environmental regulations due to release of a diester-based phthalate-based plasticizer, in particular, di(2-ethylhexyl) phthalate.

Thus, research for developing an environment-friendly plasticizer for replacing di(2-ethylhexyl)phthalate and improving the process is being conducted by many researches, in order to respond to environmental hormone problems and environmental regulations due to release of a diester-based phthalate-based plasticizer, in particular, di(2-ethylhexyl) phthalate.

DISCLOSURE

Technical Problem

An object of the present invention is to provide a method of preparing an ester-based material, which produces an environmentally friendly diester-based material as a plasticizer by a continuous process, in which productivity of a diester-based material may be improved while an amount of energy used which is supplied to a reactor is minimized, in order to solve the problems mentioned in the Background Art.

Technical Solution

In one general aspect, a method of preparing a diester-based material, which is carried out by a continuous preparation process of a diester-based material including a reaction part in which a total of n reaction units from a first reaction unit to an nth reaction unit are connected in series, the reaction unit including a reactor which esterifies dicarboxylic acid and alcohol, includes: esterifying dicarboxylic acid and alcohol in a reactor of the first reaction unit to produce a reaction product, and supplying a lower discharge stream including the reaction product to a reaction unit at a rear end, wherein an operating pressure of the reactor of the first reaction unit is 0.4 kg/cm$^2$G to 5.5 kg/cm$^2$G, an operating pressure is reduced from a reactor of any one reaction unit of reaction units from a second reaction unit to the n−1th reaction unit to a reactor of the nth reaction unit, and an operating temperature is increased from the reactor of the first reaction unit to the reactor of the nth reaction unit.

Advantageous Effects

According to the present invention, when a diester-based material is prepared by a continuous process, an operating pressure is reduced from a reactor of any one reaction unit of reaction units from a reactor of a second reaction unit to a reactor of an n−1th reaction unit to the reactor of the nth reaction unit, thereby improving productivity of the diester-based material and minimizing an amount of energy used which is supplied to the reactor.

In addition, an operating temperature of the reactor is increased toward the reaction unit at a rear end, thereby controlling a reaction rate to facilitate reaching a desired conversion rate.

DESCRIPTION OF DRAWINGS

FIGS. 1 to 2 are process flow diagrams for a method of preparing a diester-based material according to an exemplary embodiment of the present invention, respectively.

BEST MODE

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

In the present invention, the term "upper portion" means a portion corresponding to a height at or above 50% of a total height of an apparatus in a container and the term "lower portion" means a portion corresponding to a height less than 50% of a total height of an apparatus in a container or an apparatus.

The term "stream" in the present invention may refer to a fluid flow in a process, or may refer to a fluid itself flowing in a pipe. Specifically, the stream may refer to both a fluid itself flowing in a pipe connecting each device and a fluid flow. In addition, the fluid may refer to a gas, a liquid, and the like. A case in which a solid substance is included in the fluid is not excluded.

Hereinafter, the present invention will be described in more detail referring to FIGS. 1 and 2, for better understanding of the present invention.

According to the present invention, a method of preparing a diester-based material is provided. Referring to FIG. 1, the preparation method is carried out by a continuous preparation process of a diester-based material including a reaction part in which a total of n reaction units 10, 20, and no from a first reaction unit 10 to an nth reaction unit no are connected in series, the reaction unit including a reactor 11, 21, or n1 which esterifies dicarboxylic acid and alcohol, and includes: esterifying dicarboxylic acid and alcohol in a reactor 11 of the first reaction unit 10 to produce a reaction product, and supplying a lower discharge stream including the reaction product to a reaction unit at a rear end, wherein an operating pressure of the reactor of the first reaction unit is 0.4 kg/cm$^2$G to 5.5 kg/cm$^2$G, an operating pressure is reduced from a reactor of any one reaction unit of reaction units from a second reaction unit to the n−1th reaction unit to a reactor of the nth reaction unit, and an operating temperature is increased from the reactor of the first reaction unit to the reactor of the nth reaction unit.

According to an exemplary embodiment of the present invention, the diester-based material may be prepared by a continuous preparation process including a reaction part in which a total of n reaction units 10, 20, and n0 from the first reaction unit 10 to the nth reaction unit n0 are connected in series.

Specifically, conventionally, in the preparation of the diester-based material, a batch preparation process was applied. However, preparing a diester-based material by the batch process has a limitation in improvement of a reflux amount of a steam amount, has very low productivity, and has a technical limitation to be applied for improving problems.

In addition, in order to solve the problems of the batch process having the problems described above, when the diester-based material is prepared, a continuous process having a reaction part in which two or more reactors are connected in series has been developed. However, in this case, there were problems in an increase in an amount of energy used, reaching a desired conversion rate, and improving flowability.

In this regard, in the present invention, a continuous preparation process is applied to preparation of the diester-based material, thereby reducing a steam amount supplied to the reactor and facilitating reaching the desired conversion rate.

According to an exemplary embodiment of the present invention, a reactor to esterify dicarboxylic acid and alcohol may be included.

The esterification may be performed by supplying dicarboxylic acid and alcohol to the reactor and directly esterifying dicarboxylic acid and alcohol in the presence of a catalyst. As such, the diester-based material and water as a by-product are generated by the esterification of dicarboxylic acid and alcohol. An operating temperature, an operating pressure, a time, and the type and content of catalyst are applied as they are as general conditions applicable in the art, or, if necessary, may be appropriately adjusted for process operation.

The dicarboxylic acid and alcohol may be mixed by a premixer before being supplied to the reactor and introduced in batches, or may be introduced to the reactor in batches from each separate line provided.

The dicarboxylic acid may include one or more selected from the group consisting of, for example, aromatic polyvalent carboxylic acids such as phthalic acid, isophthalic acid, terephthalic acid, and trimellitic acid; and saturated or unsaturated aliphatic polyvalent carboxylic acids such as adipic acid, sebacic acid, azelaic acid, succinic acid, maleic acid, and fumaric acid. As a specific example, the dicarboxylic acid may be terephthalic acid.

The alcohol may be monohydric alcohol having 4 to 13, to 12, or 6 to 10 carbon atoms. For example, the monohydric alcohol may include linear chain or branched chain alcohol such as n-butyl alcohol, iso-butyl alcohol, secondary butyl alcohol, n-pentyl alcohol, n-hexyl alcohol, n-heptyl alcohol, n-octyl alcohol, 2-ethylhexyl alcohol, iso-octyl alcohol, iso-nonyl alcohol, n-nonyl alcohol, iso-decyl alcohol, n-decyl alcohol, undecyl alcohol, and tridecyl alcohol. As a specific example, the alcohol may be 2-ethylhexyl alcohol.

The alcohol may be supplied to the reactor in an excessive amount relative to a stoichiometric amount required for a reaction with the dicarboxylic acid. For example, a mole ratio between the dicarboxylic acid and the alcohol supplied to the reactor 11 of the first reaction unit 10 may be 1:2 to 1:5 or 1:2 to 1:4.5. Dicarboxylic acid and alcohol are supplied as reactants to the reactor 11 at a mole ratio in the range, thereby controlling a forward reaction rate of esterification while minimizing an amount of steam used to facilitate reaching a desired conversion rate. In some cases, the alcohol may be further supplied to any one or more of reactors of the reaction units from the second reaction unit 10 to the nth reaction unit n0.

The catalyst may include one or more selected from the group consisting of, for example, acid catalysts such as sulfuric acid, paratoluenesulfonic acid, and methanesulfonic acid; alkyl titanate catalysts such as tetraisopropyl titanate, tetrabutyl titanate, and tetra-2-ethylhexyl titanate; and organic metal catalysts such as dibutyl tin oxide and butyl tin maleate. As a specific example, an organic titanium compound represented by alkyl titanate may be used as the catalyst, which increases an esterification rate to shorten a reaction time.

An operating temperature of the reactor may be, for example, 130° C. to 250° C., 140° C. to 250° C., or 150° C. to 230° C. Here, the operating temperature of the reactor may refer to the temperature of each reactor in the reaction units from the first reaction unit to the nth reaction unit. More specifically, each reactor in the reaction units from the first reaction unit to the nth reaction unit may be controlled identically or separately in the temperature range.

An operating pressure of the reactor may be −1 kg/cm$^2$G to 5.5 kg/cm$^2$G, 0 kg/cm$^2$G to 4.5 kg/cm$^2$G, or 0 kg/cm$^2$G to 4 kg/cm$^2$G. Here, the operating pressure of the reactor may refer to the pressure of each reactor in the reaction units from the first reaction unit to the nth reaction unit. More specifically, each reactor in the reaction units from the first reaction unit to the nth reaction unit may be controlled identically or separately in the pressure range.

According to an exemplary embodiment of the present invention, the dicarboxylic acid may be terephthalic acid and the alcohol may be 2-hetylhexyl alcohol. As such, when terephthalic acid and 2-ethylhexyl alcohol are introduced to the reactor in the presence of a catalyst and esterified, dioctyl terephthalate (DOTP) may be prepared as the diester-based material. The dioctyl terephthalate, which is a material which is widely used as an environmentally friendly and non-toxic plasticizer, has excellent compatibility with a polymer material such as PVC and excellent properties of low volatility and electrical properties.

According to an exemplary embodiment of the present invention, the reaction part has a total of n reaction units connected in series, and may be designed considering conversion rate control of the reaction and a residence time in each unit reaction and the composition of a product to be achieved. For example, n may be 2 to 8, 3 to 7, or 4 to 6, that is, the reaction part may include 2 to 8, 3 to 7, or 4 to 6 reaction units.

According to an exemplary embodiment of the present invention, a reaction unit 10, 20, 30, 40, 50, or n0 may further include: a column 12, 22, 32, 42, 52, or n2 which is supplied with an upper discharge stream from a reactor including alcohol and water vaporized during esterification from a reactor 11, 21, 31, 41, 51, or n1 to perform gas-liquid separation, passes a gas phase through a condenser 13, 23, 33, 43, 53, or n3 as an upper discharge stream to be supplied to a layer separator 14, 24, 34, 44, 54, or n4, and supplies a liquid phase to the reactor 11, 21, 31, 41, 51, or n1 as a lower discharge stream; and a layer separator 14, 24, 34, 44, 54, or n4 which performs a separation into a water layer and an alcohol layer and refluxes only alcohol to the column while removing water.

In the reactor, the diester-based material as a reaction product and water as a by-product involved in esterification may be produced by esterification of dicarboxylic acid and alcohol. For example, the reaction product of the esterification may include the diester-based material, water, and an unreacted material.

For increasing a forward reaction rate of the esterification, water as a by-product should be effectively removed to prevent a reverse reaction and catalyst deactivation by water. In this regard, as a method of removing water which is the by-product, water is vaporized and discharged. Here, when water is vaporized, alcohol having a similar boiling point to water is also vaporized together, and the vaporized alcohol may be recovered and refluxed again to the reactor to maintain the concentration of the reactant high and water may be removed.

Specifically, in the reactor, as esterification proceeds, alcohol participates in the reaction, but alcohol which does not participate in the reaction and is vaporized due to esterification at a higher temperature than the boiling point of alcohol is inevitably present, and simultaneously, water occurs as a by-product in addition to the diester-based material as a reaction product and water may be vaporized with alcohol and discharged as the upper discharge stream from the reactor. The vaporized water and alcohol are discharged as the upper discharge stream of the reactor and may be supplied to the column.

In the column, gaseous alcohol and water introduced from the reactor may be liquefied by liquid alcohol at a low temperature supplied from the layer separator to an upper portion of the column, most of the gaseous alcohol is selectively liquefied and discharge as the lower discharge stream from the column, the lower discharge stream from the column including the liquid alcohol is introduced again to the reactor, and the liquid alcohol may participate in the esterification again. As such, by passing the upper discharge stream from the reactor through the column, water included in the upper discharge stream from the reactor is condensed and introduced to the reactor again, thereby improving a forward reaction rate.

In addition, alcohol vaporized from the reactor is refluxed to the reactor again, thereby maintaining an excessive amount ratio of alcohol in the reactor, and water as the by-product of esterification is discharged to the outside of a reaction system and removed, thereby preventing reflux of water to the reactor to prevent a reaction rate reduction and catalyst performance deterioration in the reactor.

Meanwhile, gaseous water and unliquefied gaseous alcohol in the column are discharged as the upper discharge stream from the column, and the upper discharge stream from the column passes through the condenser to be supplied to the layer separator. Specifically, the layer separator is equipment for layer-separating liquid alcohol and water, and at this point, gaseous alcohol and water need to be liquefied in the layer separator or before being introduced to the layer separator. Accordingly, a condenser is installed in an arbitrary area of a line where the upper discharge stream from the column is transferred to the layer separator, and heat of gaseous alcohol and water is removed by the condenser, thereby liquefying alcohol and water before being introduced to the layer separator.

Layer separation in the layer separator may be performed by a difference in density between alcohol and water. As a specific example, since the density of alcohol is lower than the density of water, an alcohol layer may be formed in the upper portion of the layer separator and a water layer may be formed in the lower portion. As such, after the water layer and the alcohol layer are separated in the layer separator, only alcohol may be selectively separated through a line connected to the upper portion of the column from the alcohol layer and refluxed to the column. Here, if necessary, a part of an alcohol may be removed through a line branched from a line connected to the upper portion of the column from the alcohol layer of the layer separator. In addition, water is removed through a discharge line for discharging water to the outside from the water layer or may be recycled in various routes.

Since alcohol having a lower temperature by condensation in the column is refluxed to the reactor to lower an internal temperature of the reactor, energy such as high-pressure steam or high temperature steam should be supplied for maintaining the internal temperature of the reactor to supply a heat amount into the reactor separately. Since the high-pressure steam has an equilibrium temperature (high temperature) by high pressure, a heat amount may be supplied into the reactor by supply of high-pressure steam.

The reaction product in the reactor is separated through the lower discharge stream of the reactor, the lower discharge stream in each reactor of the reaction units from the first reaction unit to the n−1th reaction unit may be supplied to the reactor of the reaction unit at the rear end of each reaction unit, and the lower discharge stream from the reactor of the reaction unit at the rearmost end may be separated and purified and productized. For example, when the diester-based material is prepared by including a reaction part in which five reaction units are connected in series, as shown in FIG. 2, a lower discharge stream from a reactor 11 of a first reaction unit 10 is supplied to a reactor 21 of a second reaction unit 20, a lower discharge stream from the reactor 21 of the second reaction unit 20 is supplied to a reactor 31 of a third reaction unit 30, a lower discharge stream from the reactor 31 of the third reaction unit 30 is supplied to a reactor 41 of a fourth reaction unit 40, a lower discharge stream from the reactor 41 of the fourth reaction unit 40 is supplied to a reactor 51 of a fifth reaction unit 50, and a lower discharge stream from the reactor 51 of the fifth reaction unit 50 may be separated and purified to be productized.

In order that the lower discharge stream from each reactor of the reaction units 10, 20, 30, 40, 50, and n0 may be transferred to the reactor of the reaction unit at a rear end or transferred to a subsequent separation purification process, a pump may be provided in a lower discharge line of each reactor.

The diester-based material included in the lower discharge stream from the reactor of the reaction unit at the rearmost end may be purified by a known method. For example, when esterification is performed by an organic titanium compound as a catalyst, water is added to the obtained diester-based material to deactivate the catalyst and then the material may be distilled with water vapor to evaporate and remove unreacted alcohol remaining therein. In addition, the material may be treated with an alkaline material to neutralize a remaining dicarboxylic acid. In addition, a solid is removed by filtration, thereby obtaining a high-purity diester-based material.

According to an exemplary embodiment of the present invention, in the continuous preparation process of a diester-based material, dicarboxylic acid and alcohol are esterified in the reactor of the first reaction unit to prepare a reaction product, and a lower discharge stream including the reaction product may be supplied to the reaction unit at the rear end through a lower discharge line.

An operating pressure of the reactor 11 of the first reaction unit 10 may be, for one example, 0.4 kg/cm$^2$G to 5.5 kg/cm$^2$G, 1 kg/cm$^2$G to 5 kg/cm$^2$G, or 1 kg/cm$^2$G to 4 kg/cm$^2$G.

Specifically, when the diester-based material is prepared, generally, the operating pressure of the reactor is operated at normal pressure for securing a reaction rate by removing water well. In this case, flow rates of water and alcohol which are vaporized to an upper portion of the reactor and discharged due to a low pressure may be increased, and thus, energy supplied to the reactor, for example, an amount of used high pressure (HP) steam, may be increased. In this regard, in the present invention, the operating pressure of the reactor 11 of the first reaction unit 10 is controlled to a high pressure within the above range, thereby lowering a flow rate of the upper discharge stream from the reactor 11 to reduce an amount of energy used which is supplied to the reactor 11. Specifically, since at the beginning of the reaction, alcohol as a reactant is injected at an excessive amount, a forward reaction is carried out well even at a high pressure, and thus, the reactor 11 is operated at a high pressure within the range at the beginning of the reaction, thereby reducing an amount of energy used which is supplied to the reactor 11.

An operating temperature of the reactor 11 of the first reaction unit 10 may be, for example, 160° C. to 210° C., 170° C. to 210° C., or 190° C. to 210° C. Since the reaction rate is high at an increased operation temperature of the reactor 11 of the first reaction unit 10, a conversion rate may be maintained high. However, when the temperature is increased excessively, a vaporization amount in the reactor and a reflux amount refluxed from the column to the reactor is increased, so that the amount of energy used is increased exponentially. Therefore, considering the conversion rate and the amount of energy used, the reactor 11 of the first reaction unit 10 may be controlled to the temperature in the above range.

According to an exemplary embodiment of the present invention, the operating pressure of the reactor of the nth reaction unit may be equal to or lower than the operating pressure of the reactor of the n−1th reaction unit. As a specific example, the operating pressure of the reactor may be reduced from the first reaction unit 10 to the nth reaction unit n0. As such, the reactor 11 of the first reaction unit 10 is operated at high pressure and the operating pressure of the reactor is reduced toward the reaction unit at the rear end, thereby removing water well toward the reaction unit at the rear end to control the reaction rate of the reactant, so that a desired conversion rate may be reached in the reactor n1 of the nth reaction unit n0 at the rearmost end.

Specifically, when the content of water in the reactor is increased, the activity of the catalyst is decreased, and the diester-based material which is the product in esterification proceeding as a reversible reaction undergoes a reverse reaction into diester-based material and alcohol, so that the entire reaction rate and conversion rate may be decreased. Therefore, when the pressure is not reduced toward to the reactor of the reaction unit at the rear end, an amount of energy used may be reduced, but removal of water and the reaction may be adversely affected. In this regard, in the present invention, the reactor of the first reaction unit is operated at high pressure to reduce the amount of energy used and also the pressure is reduced toward the reactor of the reaction unit at the rear end, thereby removing water well to solve the above problems.

The operating pressure of the reactor of the nth reaction unit may be reduced by 0% to 90%, 0% to 70%, 20% to 50%, or 0% to 50% as compared with the operating pressure of the reactor of the n−1th reaction unit.

In particular, the reactor of the reaction unit to start pressure reduction among the reactors of the reaction units from the second reaction unit 10 to the nth reaction unit n0 may be appropriately selected depending on the conversion rate. As such, the operating pressure of the reactor is controlled in each reaction unit, thereby minimizing a steam amount supplied to the reactor 11 of the first reaction unit 10 to reduce the amount of entire steam used, facilitating removal of water which is the by-product in the reactor of the reaction unit at the rear end to control the reaction rate, and facilitating reaching a desired conversion rate in the reactor n1 of the nth reaction unit n0 at the rearmost end.

According to an exemplary embodiment of the present invention, the operating temperature of the reactor of the nth reaction unit may be equal to or higher than the operating temperature of the reactor of the n−1th reaction unit. As a specific example, the operating temperature may be sequentially increased from the first reaction unit 10 to the nth reaction unit n0. As such, the reactor 11 of the first reaction unit 10 is operated at high pressure and the operating temperature of the reactor is sequentially increased toward the reaction unit at the rear end, thereby controlling the reaction rate of the reactant in the reactor of each reaction unit. For example, the operating temperature of the reactor of the nth reaction unit may be increased by 0% to 20%, 0.1% to 15%, or 1% to 5%, as compared with the operating temperature of the reactor of the n−1th reaction unit. Thus, as the reaction proceeds, the reaction rate which is lowered due to a decrease in the reactant toward the reaction unit at the rear end is improved, thereby facilitating reaching a desired conversion rate in the reactor of the reaction unit at the rearmost end.

According to an exemplary embodiment of the present invention, the operating pressure of the reactor n1 of the nth reaction unit n0 which is a reaction unit at the rearmost end may be −1 kg/cm$^2$G to 1 kg/cm$^2$G, −0.5 kg/cm$^2$G to 0.5 kg/cm$^2$G, or 0 kg/cm$^2$G to 0.2 kg/cm$^2$G, and the operating temperature thereof may be 200° C. to 250° C., 210° C. to 240° C., or 220° C. to 230° C. Specifically, in the reactor of the nth reaction unit, the desired conversion rate is in a state of being reached, in which the content of the reactant is low, water as the by-product is present, and the content of the diester-based material as the product is high, and in this case, the operating pressure and the operating temperature are controlled within the range, thereby removing water as the by-product effectively and promoting the forward reaction to facilitate reaching a desired conversion.

According to an exemplary embodiment of the present invention, the content of water in the reactor of the nth reaction unit may be decreased by 22% to 95%, 30% to 95%, or 40% to 95% as compared with the content of water in the reactor of the n−1th reaction unit. Specifically, the pressure is reduced from the reactor of the second reaction unit to the reactor of the nth reaction unit, thereby facilitating removal of water, so that the content of water in the reactor in the reaction unit may be controlled to the range described above.

According to an exemplary embodiment of the present invention, in the method of preparing a diester-based material, if necessary, devices such as a distillation column, a condenser, a reboiler, a valve, a pump, a separator, and a mixer may be further installed.

Hereinabove, the method of preparing a diester-based material according to the present invention has been described and illustrated in the drawings, but the description and the illustration in the drawings are the description and the illustration of only core constitutions for understanding of the present invention, and in addition to the process and apparatus described above and illustrated in the drawings, the process and the apparatus which are not described and illustrated separately may be appropriately applied and used for carrying out the method of preparing a diester-based material according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES AND COMPARATIVE EXAMPLES

Examples 1 to 6 and Comparative Examples 1 to 4

In the process flow diagram shown in FIG. 2, ASPEN PLUS available from Aspen Technology Inc. was used to simulate the preparation process of dioctyl terephthalate (DOTP) under the conditions of reaching a conversion rate of 99%.

Specifically, terephthalic acid and 2-ethylhexyl alcohol were introduced to the reactor 11 of the first reaction unit 10 while maintaining a mole ratio of 1:2 to 4.5 to perform esterification in the presence of a catalyst, and for the upper discharge stream vaporized in the reactor 11, alcohol was fluxed to the reactor 11 and water was removed, using the column 12, the condenser 13, and the layer separator 14. In addition, the lower discharge stream including the reaction product in the reactor 11 was supplied to the reactor 21 of the second reaction unit 20.

Like the flow of operating in the first reaction unit 10, operation was continuously performed through the second reaction unit 20, a third reaction unit 30, a fourth reaction unit 40, and a fifth reaction unit 50 and the lower discharge stream from a reactor 51 of the fifth reaction unit 50, which was at the rearmost end, was separated and purified to obtain dioctyl terephthalate.

A temperature of the reactors from the reactor 11 of the first reaction unit 10 to the reactor 51 of the fifth reaction unit 50 was controlled by gradually increasing the temperature at a temperature increase rate of 1% to 5% in a range of 196° C. to 220° C.

Here, the water content, the operating pressure, and the operating temperature in the reactors 11, 21, 31, 41, and 51 of the reaction units from the first reaction unit 10 to the fifth reaction unit 50 are shown in the following Tables 1 and 2:

TABLE 1

| | | Example | | | | | |
|---|---|---|---|---|---|---|---|
| | | 1 | 2 | 3 | 4 | 5 | 6 |
| Reactor of first reaction unit | Water content (ppm) | 2,238 | 2,238 | 2,238 | 2,238 | 4,501 | 9,713 |
| | Operating pressure (kg/cm²G) | 1 | 1 | 1 | 1 | 2 | 4 |
| Reactor of second reaction unit | Water content (ppm) | 648 | 1,316 | 1,317 | 1,046 | 2,015 | 4,313 |
| | Operating pressure (kg/cm²G) | 0.5 | 1 | 1 | 0.8 | 1.5 | 3 |
| Reactor of third reaction unit | Water content (ppm) | 493 | 493 | 1,036 | 600 | 1,037 | 2,199 |
| | Operating pressure (kg/cm²G) | 0.5 | 0.5 | 1 | 0.6 | 1 | 2 |
| Reactor of fourth reaction unit | Water content (ppm) | 208 | 207 | 208 | 131 | 207 | 600 |
| | Operating pressure (kg/cm²G) | 0.5 | 0.5 | 0.5 | 0.4 | 0.5 | 1 |
| Reactor of fifth reaction unit | Water content (ppm) | 52 | 52 | 52 | 50 | 52 | 60 |
| | Operating pressure (kg/cm²G) | 0 | 0 | 0 | 0 | 0 | 0 |
| Total amount of steam used(%) | | 58 | 52 | 50 | 50 | 45 | 36 |

TABLE 2

|  |  | Comparative Example | | | |
|---|---|---|---|---|---|
|  |  | 1 | 2 | 3 | 4 |
| Reactor of first reaction unit | Water content (ppm) | 766 | 2,238 | 4,501 | 9,713 |
|  | Operating pressure (kg/cm$^2$G) | 0.3 | 1 | 2 | 4 |
| Reactor of second reaction unit | Water content (ppm) | 388 | 1,316 | 2,745 | 6,032 |
|  | Operating pressure (kg/cm$^2$G) | 0.3 | 1 | 2 | 4 |
| Reactor of third reaction unit | Water content (ppm) | 283 | 1,036 | 2,196 | 4,866 |
|  | Operating pressure (kg/cm$^2$G) | 0.3 | 1 | 2 | 4 |
| Reactor of fourth reaction unit | Water content (ppm) | 54 | 600 | 1,430 | 3,300 |
|  | Operating pressure (kg/cm$^2$G) | 0.3 | 1 | 2 | 4 |
| Reactor of fifth reaction unit | Water content (ppm) | 49 | 459 | 1,136 | 2,690 |
|  | Operating pressure (kg/cm$^2$G) | 0.3 | 1 | 2 | 4 |
| Total amount of steam used(%) | | 100 | 43 | 33 | 29 |

Comparative Example 5 and 6

The process was performed in the same manner as in Example 1, except that ASPEN PLUS available from Aspen Technology Inc. was used to simulate the preparation process of dioctyl terephthalate (DOTP) without setting the conditions to reach a conversion rate of 99%.

The temperature of each reactor from the reactor 11 of the first reaction unit 10 to the reactor 51 of the fifth reaction unit 50 was controlled while maintaining the temperature at 215° C.

Here, the water content, the operating pressure, and the operating temperature in the reactors 11, 21, 31, 41, and 51 of the reaction units from the first reaction unit 10 to the fifth reaction unit 50 are shown in the following Table 3:

TABLE 3

|  |  | Comparative Example | |
|---|---|---|---|
|  |  | 5 | 6 |
| Reactor of first reaction unit | Water content (ppm) | 69 | 690 |
|  | Operating pressure (kg/cm$^2$G) | 0.3 | 1 |
| Reactor of second reaction unit | Water content (ppm) | 160 | 200 |
|  | Operating pressure (kg/cm$^2$G) | 0.3 | 0.5 |
| Reactor of third reaction unit | Water content (ppm) | 176 | 210 |
|  | Operating pressure (kg/cm$^2$G) | 0.3 | 0.5 |
| Reactor of fourth reaction unit | Water content (ppm) | 20 | 212 |
|  | Operating pressure (kg/cm$^2$G) | 0.1 | 0.5 |
| Reactor of fifth reaction unit | Water content (ppm) | 45 | 16 |
|  | Operating pressure (kg/cm$^2$G) | 0 | 0 |
| Total amount of steam used(%) | | 370 | 81 |

In Tables 1 to 3, the total amount of steam used was measured as the total amount of steam used each of Examples 1 to 6 and Comparative Examples 1 to 6, and is shown by converting the amount into a percentage with respect to the total amount of steam used in Comparative Example 1.

Referring to Tables 1 to 3, in the continuous preparation process of the diester-based material, it was seen that in Examples 1 to 6, the operating pressure of the reactor, the water content, and the operating temperature in each reaction unit were controlled as described above, whereby the sum of the total amount of steam used which is supplied to the reactor to the entire reaction units is about 36% to 58% relative to Comparative Example 1 which is low.

In particular, it was confirmed that in Examples 4 to 6 in which the operating pressure of the reactor 11 of the first reaction unit 10 was controlled to 1 kg/cm$^2$G to 4 kg/cm$^2$G, the operating temperature was sequentially increased toward the reactor of the reaction unit at a rear end, and the operating pressure was sequentially reduced, water may be effectively removed, and the total amount of steam used was lower.

In contrast, it was confirmed that in Comparative Example 1 in which the operating pressures of the reactors in the reaction units from the first reaction unit 10 to the fifth reaction unit 50 were all controlled to 0.3 kg/cm$^2$G, an amount of steam supplied to the reactor of the entire reaction units was high due to low-pressure operation.

In addition, it was confirmed that in Comparative Examples 2 to 4 in which the operating pressures of the reactors in the reaction units from the first reaction unit 10 to the fifth reaction unit 50 were all controlled to 1 kg/cm$^2$G, 2 kg/cm$^2$G, and 4 kg/cm$^2$G, respectively, the total amount of steam supplied to the entire reaction units was similar to the examples due to high-pressure operation, but water was not removed well in the reaction unit at the rear end, so that the water content in the reactor was high.

In addition, it was confirmed that the reactor 11 of the first reaction unit 10 was operated at a low pressure, and the operating pressure was reduced toward the reactor of the reaction unit at the rear end, but in Comparative Example 5 in which the operating temperature was maintained, the total amount of steam used was 370 times Comparative Example 1.

In addition, in Comparative Example 6 in which the reactor 11 was operated at high pressure in the first reaction unit 10, and the operating pressure was reduced toward the reactor of the reaction unit at the rear end, but the temperature was maintained to be constant also, the total amount of steam used was increased as compared with the examples, and 70% or more of the entire amount of steam used was used in the reactor 11 of the first reaction unit 10. In this case, since energy used for increasing the temperature of a raw material at a low temperature to the reaction temperature and vaporizing the material was large, the reactor 11 of the reaction unit 10 should be inefficiently large.

The invention claimed is:

1. A method of preparing a diester-based material, which is carried out by a continuous preparation process of a diester-based material including a reaction part in which a total of n reaction units from a first reaction unit to an nth reaction unit are connected in series, the reaction unit including a reactor which esterifies dicarboxylic acid and alcohol in the presence of a catalyst, the method comprising:

esterifying dicarboxylic acid and alcohol in a reactor of the first reaction unit to produce a reaction product, and supplying a discharge stream from a lower portion of the reactor including the reaction product to a reaction unit at a rear end, wherein an operating pressure of the reactor of the first reaction unit is 0.4 kg/cm$^2$G to 5.5 kg/cm$^2$G, an operating pressure is reduced from a reactor of any one reaction unit of reaction units from a second reaction unit to the nth reaction unit to a reactor of the nth reaction unit, an operating temperature is increased from the reactor of the first reaction unit to the reactor of the nth reaction unit, and wherein the dicarboxylic acid includes terephthalic acid and the alcohol includes 2-ethylhexyl alcohol and the catalyst includes organic titanium compound.

2. The method of preparing a diester-based material of claim 1, wherein an operating pressure of the reactor of the nth reaction unit is equal to or lower than an operating pressure of a reactor of an n−1th reaction unit.

3. The method of preparing a diester-based material of claim 2, wherein the operating pressure of the reactor of the nth reaction unit is decreased by 0% to 90% as compared with the operating pressure of the reactor of the n−1th reaction unit.

4. The method of preparing a diester-based material of claim 1, wherein the operating pressure of the reactor of the first reaction unit is 0.4 kg/cm$^2$G to 4 kg/cm$^2$G.

5. The method of preparing a diester-based material of claim 1, wherein the operating temperature of the reactor of the first reaction unit is 160° C. to 210° C.

6. The method of preparing a diester-based material of claim 1, wherein the operating temperature of the reactor of the nth reaction unit is increased by 0% to 20% as compared with the operating temperature of the reactor of the n−1th reaction unit.

7. The method of preparing a diester-based material of claim 1, wherein the operating pressure of the reactor of the nth reaction unit is −1 kg/cm$^2$G to 1 kg/cm$^2$G, and the operating temperature thereof is 200° C. to 250° C.

8. The method of preparing a diester-based material of claim 1, wherein a water content in the reactor of the nth reaction unit is decreased by 20% to 95% as compared with a water content in the reactor of the n−1th reaction unit.

9. The method of preparing a diester-based material of claim 1, wherein n is 2 to 8.

10. The method of preparing a diester-based material of claim 1, wherein a mole ratio between an amount of the dicarboxylic acid introduced and a total amount of alcohol introduced to the reactor of the first reaction unit is 1:2 to 1:5.

11. The method of preparing a diester-based material of claim 1, wherein the reaction unit further includes:

a column which is supplied with an upper discharge stream from the reactor including alcohol and water vaporized during esterification from the reactor to perform gas-liquid separation, passes a gas phase through a condenser as the upper discharge stream to be supplied to a layer separator, and supplies a liquid phase to the reactor as a lower discharge stream; and a separator which performs a separation into a water layer and an alcohol layer and refluxes only alcohol to the column while removing water.

* * * * *